United States Patent
Hempel (10) Patent No.: US 7,535,986 B2
(45) Date of Patent: May 19, 2009

(54) METHOD AND CT SYSTEM FOR DETECTING AND DIFFERENTIATING PLAQUE IN VESSEL STRUCTURES OF A PATIENT

(75) Inventor: Eckhard Hempel, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 128 days.

(21) Appl. No.: 11/700,058

(22) Filed: Jan. 31, 2007

(65) Prior Publication Data
US 2007/0183558 A1    Aug. 9, 2007

(30) Foreign Application Priority Data

Feb. 1, 2006   (DE) .................. 10 2006 004 604
Feb. 1, 2006   (DE) .................. 10 2006 004 976
Jul. 31, 2006  (DE) .................. 10 2006 035 677

(51) Int. Cl.
     *A61B 6/00*    (2006.01)
(52) U.S. Cl. ............................ 378/4; 382/131
(58) Field of Classification Search ............ 378/4–20, 378/901; 382/130, 131, 132
See application file for complete search history.

(56) References Cited

U.S. PATENT DOCUMENTS 6,922,462 B2 *   7/2005   Acharya et al. ......... 378/98.11

2004/0136491 A1   7/2004   Iatrou et al.

FOREIGN PATENT DOCUMENTS

EP        1 447 046 A1    8/2004

OTHER PUBLICATIONS

Siemens AG, Medical Solutions, Roland Fath: "The Fast Lane to Diagnosis", Jun. 2005, pp. 28-31.
Joseph Schoepf: "Thorax imaging fulfills promise with computer-aided detection", Computed Tomography, Diagnostic Imaging, Nov. 2005, pp. 105-114.
Weitkamp, Timm et al.: "X-ray phase imaging with a grating interferometer", Optics Express, vol. 13, No. 16, published Aug. 8, 2005, pp. 6296-6304.

* cited by examiner

*Primary Examiner*—Courtney Thomas
(74) *Attorney, Agent, or Firm*—Harness, Dickey & Pierce, P.L.C.

(57) ABSTRACT

A method and a CT system are disclosed for detecting and differentiating plaque in vessel structures of a patient. In at least one embodiment, a computed tomography system that is equipped with at least one focus detector system and, per focus detector system, with at least one transradiated x-ray/optical grating, is used to reconstruct the spatial distribution of the refractive index in the region of vessel structures of the patient from detected projection data. Further, at least one plaque form is highlighted in a pictorial display on the basis of a previously known value range of the refractive index for at least one plaque form.

27 Claims, 5 Drawing Sheets

METHOD AND CT SYSTEM FOR DETECTING AND DIFFERENTIATING PLAQUE IN VESSEL STRUCTURES OF A PATIENT

PRIORITY STATEMENT

The present application hereby claims priority under 35 U.S.C. §119 on German patent application numbers DE 10 2006 004 604.8 filed Feb. 1, 2006, DE 10 2006 004 976.4 filed Feb. 1, 2006, and DE 10 2006 035 677.2 filed Jul. 31, 2006, the entire contents of each of which is hereby incorporated herein by reference.

FIELD

Embodiments of the invention generally relate to a method for detecting and differentiating plaque in vessel structures of a patient with the aid of a computed tomography system, and/or to a computed tomography system for carrying out this method.

BACKGROUND

Methods for detecting and differentiating plaque in vessel structures of patients with the aid of absorption computed tomography, and absorption CT systems used therefor are generally known in principle. For the most part, in this case contrast media are applied so as to display the vessel structures, and the presence of plaque is determined by more thoroughly viewing the edge region of the displayed vessels with absorption data. There are also attempts at determining the different consistency of plaque, calcified or soft, with the aid of absorption CT. Calcified plaque generally does not constitute a health risk, while so called soft plaque conceals a greatly increased risk of cardiac infarction. However, in determining and in particular in classifying plaque the problem arises that the absorption differences of different plaque types turn out to be relatively slight.

Two effects can be considered in principle for imaging by way of ionizing beams, in particular x-ray beams which occur when the radiation penetrates matter and are, specifically the absorption and the phase shift of the radiation penetrating an examination object.

Such phase contrast radiography or phase contrast tomography requires the phase shift caused by the object to be evaluated. By analogy with conventional absorption contrast x-ray radiography or absorption contrast x-ray tomography, it is possible both to prepare projected images of the phase shift, and to calculate tomographic displays of the phase shift from a multiplicity of projective images.

Such phase shifts can be determined by the use of interferometric gratings, and be used to produce projective or tomographic images. Reference may be made to the previously cited documents as regards this interferometric measuring method. In the case of this method, an examination object is transradiated by a coherent or quasi-coherent x-radiation and is subsequently guided through a phase grating of a period adapted to the wavelengths of the radiation, as a result of which there is firstly beam splitting, and there results from the position of the divided beams an interference pattern that is modulated by the phase shift modulating from the object. This interference pattern is measured by means of a subsequent analyzer detector arrangement such that the phase shift can be determined for each "beam" or each detector element that generates an image pixel. This can be performed either by a number of measurements with offset analyzer gratings or by direct determination of the phase shift with the aid of a detector element that is subdivided at least in a threefold fashion perpendicular to the line orientation of the grating lines of the phase grating.

With regard to the refractive index, which is given for x-ray beams by $$n = 1 - \delta - i\beta,$$

the absorption is a function of the magnitude of the imaginary decrement with $\beta$, which is related to the mass absorption coefficient $\mu/\rho$ $$\mu/\rho = 4\pi\beta/\lambda,$$

$\lambda$ being the wavelength, $\mu$ being the linear absorption coefficient, and $\rho$ being the mass density.

The phase shift follows from the real part of the refractive index $1-\delta$. The phase shift $\Delta$ of an x-ray wave in matter is given, in comparison with a vacuum, by $$\Delta = 2\pi\delta T/\lambda,$$

T being the thickness of the matter and $\delta$ the real decrement of the refractive index.

Phase contrast tomography requires evaluation of the phase shift caused by the object. By analogy with the absorption CT, it is possible to calculate from projection data a three-dimensional data record that shows the spatial distribution of the real part of the refractive index $1-\delta$.

Since the phase of a wave cannot be measured directly, the first requirement is to convert the phase shift into a measurable intensity by way of the interference between the wave to be examined and a reference wave. Carrying out such measurements in practice, both with reference to projective images and with reference to tomographic images is, for example, in European patent application EP 1 447 046 A1 and in the German patent applications with the file references 10 2006 017 290.6, 10 2006 015 358.8, 10 2006 017 291.4, 10 2006 015 356.1 and 10 2006 015 355.3.

In the context of the patent application, reference is often to be made to the following state of affairs relating to the problems of "coherent x-radiation", "coherent x-radiation sources" and "quasi-coherent x-radiation sources":

The emission of x-ray photons via laboratory x-ray sources (x-ray tubes, secondary targets, plasma sources, radioactive sources, parametric x-ray sources, channeling radiation), and also of conventional synchrotron radiation sources of first to third generation is subject to stochastic processes. The emitted x-radiation therefore has no special coherence per se. The radiation of x-ray sources behaves, like spatially coherent radiation in phase contrast radiography and tomography when the viewing angle at which the source appears to the viewer or the object, the grating or the detector is sufficiently small. The so called lateral coherence length L:

$$L = \lambda \frac{a}{s}.$$

may be specified as a measure of the spatial coherence of an extended x-ray source. Here, $\lambda$ is the wavelength, s the transverse source size, and a the source/viewer distance. Some authors also designate half the above defined value as spatial coherence length. The exact value is secondary; what is important is that the coherence length L be large by comparison with the (lateral) dimensions of the spatial region from which beams are to interfere with one another.

For the purpose of the patent application, coherent radiation is understood to be a radiation that leads to the formation of an interference pattern under the given geometries and distances from the desired x-ray/optical grating. It is self evident that the spatial coherence, and thus the spatial coherence length, are always determined by the triplet of variables comprising wavelength, source size and viewing distances. For the purpose of a compact formulation, this state of affairs has been shortened to expressions such as "coherent x-radiation" "coherent x-radiation source" or "point source for generating a coherent x-radiation". These abbreviations are based on the fact that the wavelength of the energy E of the x-radiation in the application discussed here is limited by the desired penetrating power of the examination object, on the one hand, and the spectrum available in the case of laboratory x-ray sources. The distance a between source and observer is also subject to certain restrictions in medical diagnostics. The last degree of freedom therefore usually remains the source size s, even when the relationships between source size and tube power set narrow limits here.

The source grating permits the use of greater and thus more powerful x-ray sources.

The narrow slits of the source grating ensure observance of the required spatial coherence of all the beams that emerge from one and the same slot. Only photons from one slot can interfere with one another, that is to say they superpose with correct phase. Although no correctly phased superposition is possible between the photons from slit to slit of the source grating, with suitable tuning of the source grating period $d_0$ and the interference pattern period $d_2$ as well as the distance 1 between the source grating $G_0$ and phase grating $G_1$, and the distance d between the phase grating $G_1$, and the interference pattern $G_2$ in accordance with $g_0/g_2=1/d$, correct superposition of the wave antinodes and the wave nodes of the standing wave field is possible at least in terms of intensity. In the abbreviated formulation of the patent application, the term "quasi-coherent radiation" or "quasi-coherent radiation source" is used in this context.

The temporal or longitudinal coherence of the radiation is associated with the monochromaticity of the x-radiation or the x-radiation source. The x-radiation of intense characteristic lines usually has a sufficient monochromaticity or temporal coherence length for the applications discussed here. Upstream monochromators or selection of the resonant energy via the web height of the phase grating can also filter out a sufficiently narrow spectral range from a Bremsstrahlung spectrum or synchrotron spectrum, and thus satisfy the requirements for the temporal coherence length in the present arrangements.

SUMMARY

In at least one embodiment of the invention, a method and a corresponding CT system are included that permit plaque to be detected and reliably differentiated in the region of a vessel structure of a patient, in particular also in the coronary region.

Consequently, the inventor, in at least one embodiment, proposes both a method and a CT system for detecting and differentiating plaque in vessel structures of a patient.

In accordance with at least one embodiment of the inventive method, a computed tomography system that is equipped with at least one focus detector system and with at least one transradiated x-ray/optical grating per focus detector system is used to reconstruct the spatial distribution of the refractive index in the region of vessel structures of the patient from detected projection data (=phase contrast measurement), and to highlight at least one plaque form in a pictorial display on the basis of a previously known value range of the refractive index for at least the plaque form.

In accordance with a development of this at least one embodiment of the method, it is also possible for different plaque forms to be associated with different value ranges of the refractive index, and to be differently highlighted. This can be done, for example, in that during image processing the refractive indices present as sectional images or volume data are compared with a look up table in which there are specified for the refractive indices the value ranges that are assigned to specific types of plaque. When corresponding values are found, the corresponding pixels or voxels can be highlighted, for example by setting a color code or by means of another marking.

In a particular design of at least one embodiment of the method, use is made of at least two focus detector systems arranged on a gantry in an annularly offset fashion. It is possible as a result, for example, to achieve higher scanning frequencies, or simultaneously to apply different x-ray energies for different focus detector systems, respectively for absorption measurements and/or phase contrast measurements.

Moreover, one focus detector system can sweep a smaller fan angle than another focus detector system, and the phase contrast measurement is carried out with a higher spatial resolution with the aid of a focus detector system with a smaller fan angle than with the aid of the focus detector system with a larger fan angle.

In order to generate quasi-coherent x-radiation in conjunction with a sufficiently high dose rate for a medical examination, it is possible to use in at least one of the focus detector systems, preferably in the focus detector system with a large fan angle, at least one source grating between focus and patient for the purpose of generating quasi-coherent x-radiation.

Furthermore, in at least one of the focus detector systems use is made of an analyzer detector system that has an analyzer grating. In this embodiment, the analyzer grating is displaced in small steps relative to the detector, and the phase shift of the respective beam is determined by measuring the radiation intensity relative to the grating offset.

Alternatively, in order to measure the phase shift it is also possible in at least one of the focus detector systems to use an analyzer detector system that has a detector whose resolution is higher than the resolution of the measured pixels. The phase shift can thereby be determined by a single measurement.

It is also proposed according to at least one embodiment of the invention to detect plaque and/or its formations by comparing absorption data with refractive index data. Thus, both absorption coefficients and refractive indices are measured in a spatially resolved fashion by way of simultaneous or temporarily offset scans, and the presence of plaque and the type of plaque are inferred, from the comparison or the combination of absorption data and refractive index.

It can be advantageous thereby when the spatial distribution of the refractive indices is exclusively measured with a focus detector system, and the spatial distribution of the absorption coefficients is exclusively measured with another focus detector system. However, it should be pointed out that absorption data can also be determined when measuring the phase contrast by integrating individual measurements relating to the phase determination.

In a further design of at least one embodiment of the method according to the invention, the inventor proposes that the phase contrast measurement be executed for at least two different x-ray energies. A further improved analysis of plaque is rendered possible thereby. In particular, by using energies that respond with particular specificity to calcium inclusions in plaque—the calcium of the plaques includes for the most part of calcium hydroxyl apatite—it is possible to determine the degree of calcification in the plaque, and thereby to distinguish between calcified plaque and soft plaque.

Again, the absorption measurement can be executed for at least two different x-ray energies, as a result of which the localization of plaque can likewise be facilitated, and the different forms of plaque can be differentiated subsequently by way of phase contrast differences in the regions thus localized.

It may also be mentioned by way of supplement that the measurements with different x-ray energies can be executed simultaneously with at least two focus detector systems.

Finally, it remains to mention that at least one of the measurements, specifically absorption measurement and/or phase contrast measurement, can, or should be, carried out in a fashion triggered by the cardiac movement, use being made for visualization only of data in the rest phase of the heart.

According to at least one embodiment of the inventive method, the inventor also proposes a computed tomography system (CT system) for detecting and differentiating plaque in vessel structures of a patient by way of phase contrast measurements, the CT system having:

at least one focus detector system for generating and detecting x-radiation;
at least one focus detector system with at least one transradiated x-ray/optical grating,
at least one analyzer detector system for measuring the phase shift of impinging radiation,
an arithmetic and control system for controlling the CT system and reconstructing and evaluating the measured results,
an output unit for outputting sectional or volume data,
a memory with a look up table for comparing the distribution, measured by the phase contrast measurement and reconstructed spatially, of refractive indices with stored value ranges and related plaque forms, and
a marking apparatus that marks on the output sectional and volume data regions whose refractive indices lie in the value range for at least one plaque form.

It is preferable for there to be present in the memory of the computer system of such a CT system program code that detects different plaque forms on the basis of different value ranges of the refractive index, and displays them in the differently highlighted fashion.

In a particular design, such a CT system can have two focus detector systems arranged on a gantry in an angularly offset fashion, in which case it is possible in an example configuration for a first focus detector system to have a smaller fan angle than the second focus detector system, and the first focus detector system has a higher resolution analysis detector system, referred to the angular resolution, than the second focus detector system.

Moreover, at least one embodiment of the inventive CT system can have a first focus detector system with a smaller fan angle than the second focus detector system, and only the first focus detector system has an analysis detector system, whereas the second focus detector system is free from x-ray/optical gratings and serves only for measuring absorption data.

It can also be advantageous to equip a first focus detector system with a substantially smaller focus than the second focus detector system. It is possible thereby to generate with the aid of the small focus a quasi-coherent x-radiation that is required for the phase contrast measurement. Alternatively, it is also possible to equip at least one focus detector system with at least one source grating between focus and patient in order to generate quasi-coherent x-radiation.

Furthermore, at least one focus detector system of the CT system can have an analyzer detector system that has an analyzer grating. Likewise, in at least one focus detector system there can be present an analyzer/detector system that has a detector whose angular resolution (measured in points/angle) perpendicular to the grating lines of the phase grating is at least three times as high as the resolution in the direction of the grating lines.

In order to achieve a CT system that is as flexible as possible and can easily be tuned to different x-ray energies, it is also possible for at least one focus detector system to have an x-ray/optical grating whose grating lines are produced by standing ultrasonic waves.

Furthermore, for reasons of simple and cost effective production at least one focus detector system can have an x-ray/optical grating that includes a number of similar gratings arranged directly in sequence.

BRIEF DESCRIPTION OF THE DRAWINGS

The invention is described in more detail below with reference to the example embodiments and with the aid of the figures, only the features necessary for understanding the invention being illustrated. The following reference symbols are used in this case: 1: CT system; 2: first x-ray tube; 3: first detector; 4: second x-ray tube; 5: second detector; 6: gantry housing; 7: patient; 8: patient couch; 9: system axis; 10: control and arithmetic unit; 11: memory; 12: image detail from sectional image; 13: coronary structure; 14: plaque, calcified; 15: plaque, soft; 16: plaque, calcified; A, B: measuring paths; d, $d_1$, $d_2$: distance between phase grating and analyzer grating; dN/N: differential photon flux; $D_1$, $D_2$: detector; $E_i$: ith detector element; $F_1$, $F_2$: focus; $G_0$, $G_{01}$, $G_{02}$: source gratings; $G_1$, $G_{11}$, $G_{12}$: phase gratings; $G_2$, $G_{21}$, $G_{22}$: analyzer gratings; $h_0$, $h_1$, $h_2$, $h_{11}$, $h_{12}$: height of the grating webs; $I(E_i(X_g))$: measured intensity at the detector element Ei with a grating offset of $x_G$; I: intensity of the photon flux; $I_{ph}$: pictorial display by way of phase contrast measurement; $I_A$ pictorial display by way of absorption measurement; $I_{Ph,A}$: synopsis from the pictorial display by way of phase contrast measurement and absorption measurement; 1, $1_1$, $1_2$: distance between source grating and phase grating; n: refractive index; P: patient; $P_0$, $P_1$, $P_2$: period of the grating lines; $P_{DS}$: period of the scintillation strips; $Prg_n$: program; S: system axis; $S_i$: x-ray beams; $SS_{x_i}$: scintillation strips; w: extent of the focus; $X_G$: offset of the analyzer grating; μ: absorption coefficients; λ, λi: wavelength of the x-radiation viewed; φ: phase shift.

In detail.

DETAILED DESCRIPTION OF THE EXAMPLE EMBODIMENTS

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

Figure 1:
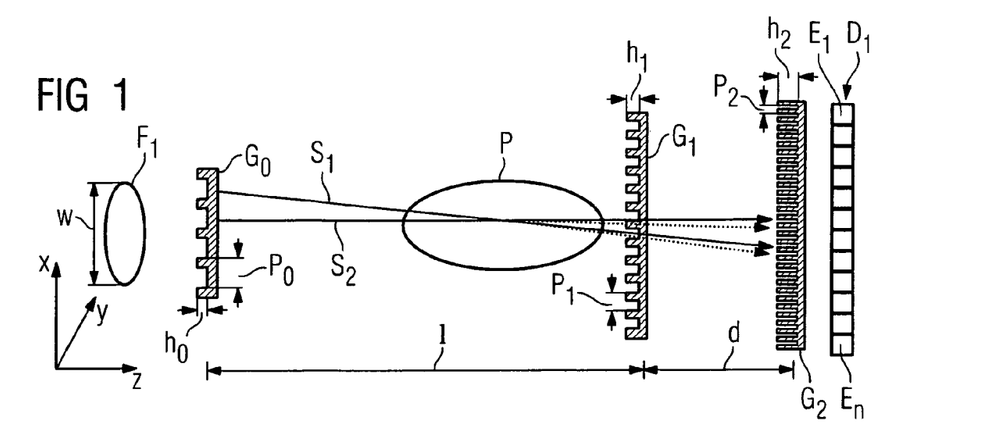
FIG. 1 shows a longitudinal section through a focus detector system, displaying source grating, phase grating and analyzer grating and their grating structure.

A focus detector system having a grating set $G_0$ to $G_2$ is shown schematically in FIG. 1 for the purpose of a better understanding of phase contrast measurement. Located upstream of the first grating $G_0$ is the focus $F_1$, whose greatest extent is noted by w. The first grating $G_0$ has a period $P_0$ of the grating line and a height $h_0$ of the grating webs. Correspondingly, the gratings $G_1$ and $G_2$ are also provided with a height $h_1$, and $h_2$, respectively, and a period $P_1$ and $P_2$, respectively. The function of phase measurement requires that the distance l between the grating $G_0$ and the grating $G_1$, and the distance d between the grating $G_1$ and the grating $G_2$ be at a specific ratio to one another. It holds in this case that $$P_0 = P_2 \times \frac{1}{d}$$

The distance of the detector $D_1$ with its detector elements $E_1$ to $E_n$ from the last grating $G_2$ is of no importance. The height $h_1$ of the webs of the phase grating should be selected in this case such that the following formula holds:

$$h_1 = \frac{\lambda}{2(n-1)}$$

in accordance with the wavelengths considered, that is to say the energy of the x-radiation that is considered, and with reference to the respective grating material. Here, n denotes the refractive index of the grating material, and λ the wavelengths of the x-ray beams for which the phase shift is to be measured.

This grating can advantageously be set to an energy that corresponds to a characteristic line in the x-ray spectrum of the anode being used; a sufficient photon number at least, should be available in this energy range. The $K_\alpha$ line, for example, can be used with the currently customary tungsten anode. However, there is also the possibility of using the $K_\beta$ line lying close thereto. Other energies and thus other dimensions of the phase grating become necessary for selecting other anode materials.

The height $h_2$ of the analyzer grating must be sufficient to produce effective absorption differences between the webs transradiated by the x-radiation, and the largely free sites of the grating, so as to provide a corresponding Moiré pattern on the rear side.

The line orientation of the gratings $G_0$ to $G_2$ is regularly designed such that the grating lines of all three gratings run parallel to one another. Furthermore, it is advantageous, but not necessary, when the grating lines are oriented parallel or perpendicular to the system axis S, the gratings $G_0$ to $G_2$ mostly being of planar formation and being aligned perpendicular to the center line between the focal point and detector midpoint. However, there is also the possibility in principle of adapting the surfaces of the grating to the optical path of the light cone such that at each location the gratings are intersected perpendicularly by the beam connection between the focus and the respective detector element, the result of this being a corresponding curvature of the gratings.

Figure 2:
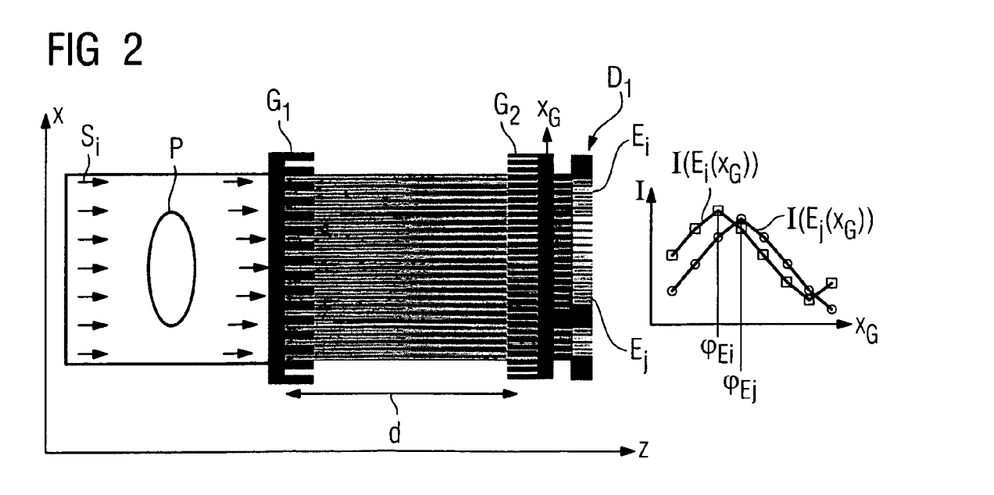
FIG. 2 shows a longitudinal section through a focus detector system of a CT having a phase grating, analyzer grating and detector for displaying the interference phenomenon.

The individually coherent radiation that is incident from the grating $G_0$ and penetrates the patient P is shown once again in FIG. 2, phase shift phenomena coming about after the penetration of the patient P. As a result, when the grating $G_1$ is penetrated an interference pattern that is illustrated by the gray shading is produced and leads with the aid of the grating $G_2$ on the adjoining detector $D_1$ and its detector elements to different radiation intensities per detector element, a so-called Moiré pattern also being formed there.

If, for example, the detector element $E_i$ is considered as a function of an offset $X_G$ of the analyzer grating $G_2$, and if the intensity $I(E_i(X_G))$ is plotted as a function of the offset $X_G$ against the intensity I, the result is a sinusoidal rise and fall in the intensity I at this detector element $E_i$. If this measured radiation intensity I is plotted for each detector element $E_i$ or $E_j$ as a function of the offset $x_G$, the result of this for the various detector elements, which finally, after all, constitute the spatial x-ray beam between the focus and the respective detector element, is the possibility of determining the phase shift $\phi$ relative to one another for each detector element. It holds that:

$$\varphi = 2\pi n \frac{v}{\lambda},$$

v corresponding to the size of voxel or pixel in the object examined, n being the refractive index thereof, and $\lambda$ representing the wavelength of the x-radiation.

It is possible in this way to determine the phase shift per beam by way of at least three measurements with in each case an offset analyzer grating for each beam in the space and from this either it is possible in the case of projective x-ray images to calculate the pixel values of a projective image directly, or projections are prepared in the case of a CT examination whose pixel values correspond to the phase shift such that with the aid of reconstruction methods known per se it can be calculated therefrom which volume element in the examination object is to be ascribed to which part at the measured phase shift. Either sectional images or volume data that reflect the spatial effect of the object examined with reference to the phase shift of an x-radiation are therefore calculated therefrom. Since even slight differences in composition exert a strong effect on the phase shift, it is possible thereby to return very detailed and contrasting volume data of materials that are relatively similar per se, in particular of soft tissue.

In the case of the abovedescribed variant of the detection of phase shifts in x-ray beams that penetrate an examination object with the aid of a multiply offset analyzer grating and measurement of the radiation intensity on the detector element downstream of the analyzer grating, there is the disadvantage of needing to carry out at least three measurements of each x-ray beam with the analyzer grating displaced in each case. The scanning of the examination object is thereby rendered relatively slow, the dose commitments simultaneously increasing. There is the additional problem that because of the analyzer grating used a portion of the radiation is lost to the detection, since it is absorbed in the grating.

Alternatively, it is possible to dispense with such an analyzer grating and, instead, to structure the detector elements that are arranged following the phase grating in such a way that at least there is no dose loss during measurement. It is preferably possible to select a split by which the phase shift in the beam being viewed can be determined with the aid of a single measurement.

Figure 3:
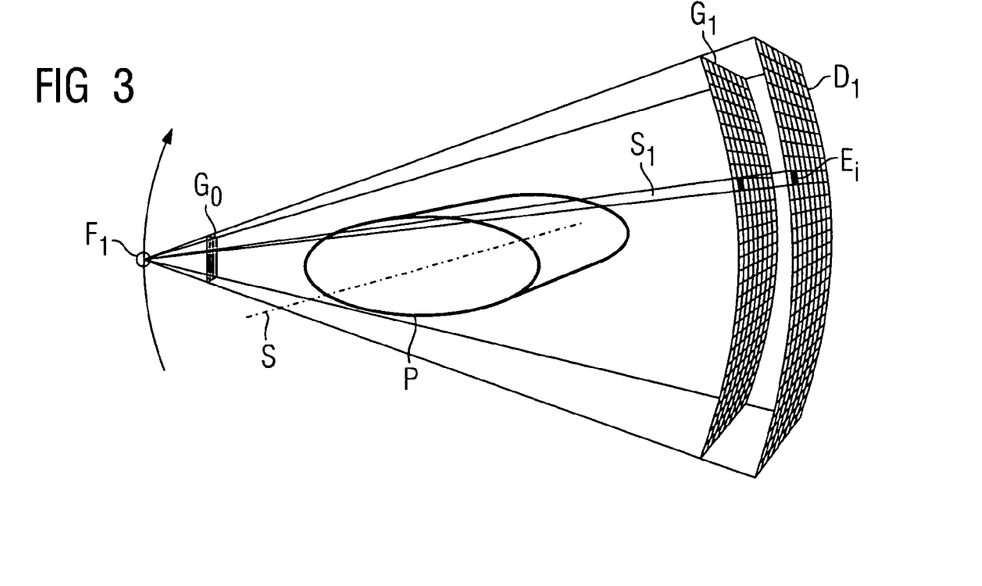
FIG. 3 shows a 3D schematic of an embodiment of an inventive focus detector system without analyzer grating.

Such a focus detector arrangement is shown schematically in a 3D illustration of a focus detector system of a computed tomograph in FIG. 3. This shows a focus $F_1$ in whose beam path a source grating $G_0$ is arranged and there is present on the detector side a phase grating that produces the previously described interference phenomena that are measured by the downstream detector such that each individual detector element can measure the phase shift, more accurately the mean phase shift, in the radiation via this detector element. Represented on the detector side in the illustration shown is a detector $D_1$ that is designed as a multirow detector, each row containing a multiplicity of detector elements, and a grating structure of the phase grating $D_1$ being positioned upstream of each detector element.

Figure 4:
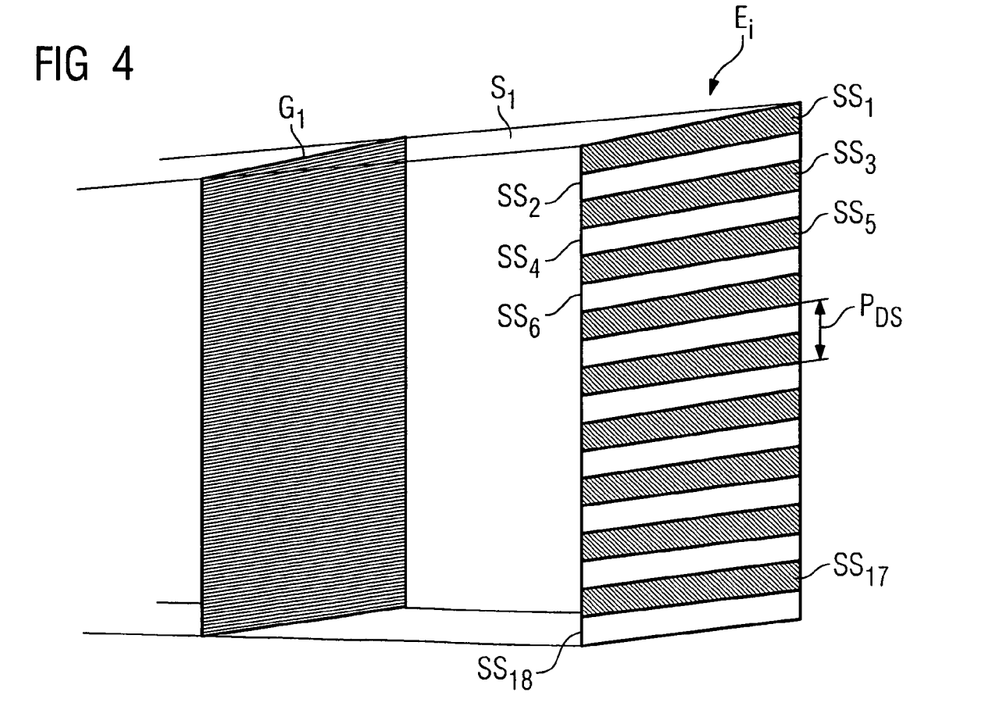
FIG. 4 shows a three-dimensional illustration of a single detector element with an upstream phase grating.

This combination between grating and detector element is shown in an enlarged fashion in FIG. 4. The detector element is illustrated here in structured fashion, and it comprises a multiplicity of scintillation strips $SS_1$ to $SS_{18}$ that are oriented in terms of their alignment in a fashion parallel to the grating lines of the phase grating $G_1$. It may be pointed out in this case that the split shown here is merely a schematic illustration intended to show the basic principle of the split, the proportions differing fundamentally in practice from the illustration.

In practice, the size of such a detection element is in the range from 100 to 1000 µm. The period $P_2$, in the order of magnitude of which the extent of the scintillation strips $SS_1$, to $SS_{18}$ must lie is generally approximately 2 µm, and so the individual scintillation strips are about 1 µm should they be split into two divisions. If a higher split is selected, the width of the scintillation strips is reduced correspondingly by, for example, half a µm, the width of the scintillation strips being, in turn, a function of the selected energy for which the phase shift is to be measured.

Figure 5:
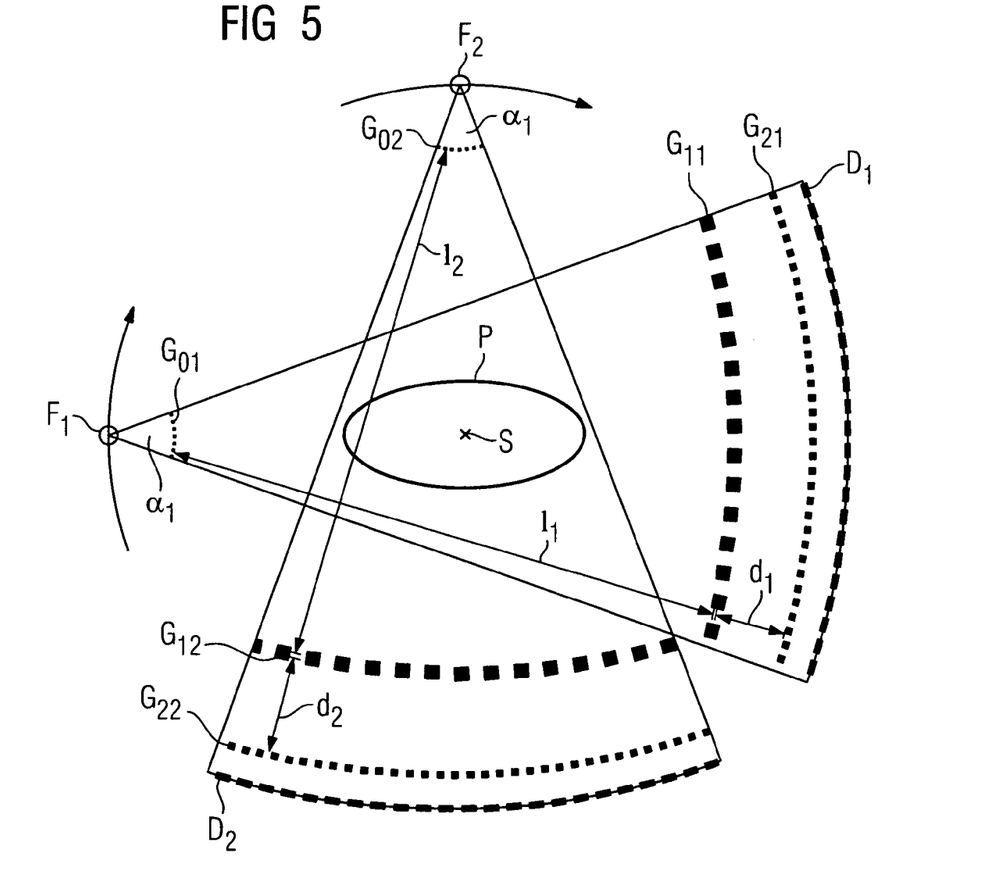
FIG. 5 shows a schematic sectional illustration of two focus detector systems, offset by 90°, of a CT having different grating sets.

A further example design of two focus detector systems $F_1$, $D_1$ and $F_2$, $D_2$, arranged with an angular offset in an inventive CT system is shown in cross section in FIG. 5 in a schematic illustration. The two focus detector systems are located on a common gantry and are rotated at the same speed about the examination object, here about a patient P, while the patient P is preferably advanced in the direction of the system axis S such that a spiral scanning results. Arranged in the two focus detector systems $F_1$, $D_1$ and $F_2$, $D_2$ are respectively different grating sets $G_{01}$, $G_{11}$, $G_{21}$ and $G_{02}$, $G_{12}$, $G_{22}$, which also have different distances $d_1$, $l_1$ and $d_2$ and $l_2$.

The web heights of the phase gratings are also adapted in accordance with the desired radiation energy to be examined and for which the phase shift is measured. The patient P can in this way be scanned simultaneously with reference to different energy-dependent phase shifts, there being no restriction with reference to the use of different acceleration voltages in the two focus detector systems $F_1$, $D_1$ and $F_2$, $D_2$. It is to be pointed out in this case that absorption data with the aid of which absorption volume data can respectively be reconstructed are also respectively available on the basis of the phase contrast measurements.

The fan angles of the focus detector systems are denoted by $a_1$, and $a_2$. In the case illustrated, $a_1=a_2$, but it is also possible to select fan angles of different size, it preferably being possible to select a higher angular resolution for smaller fan angles.

Figure 6:
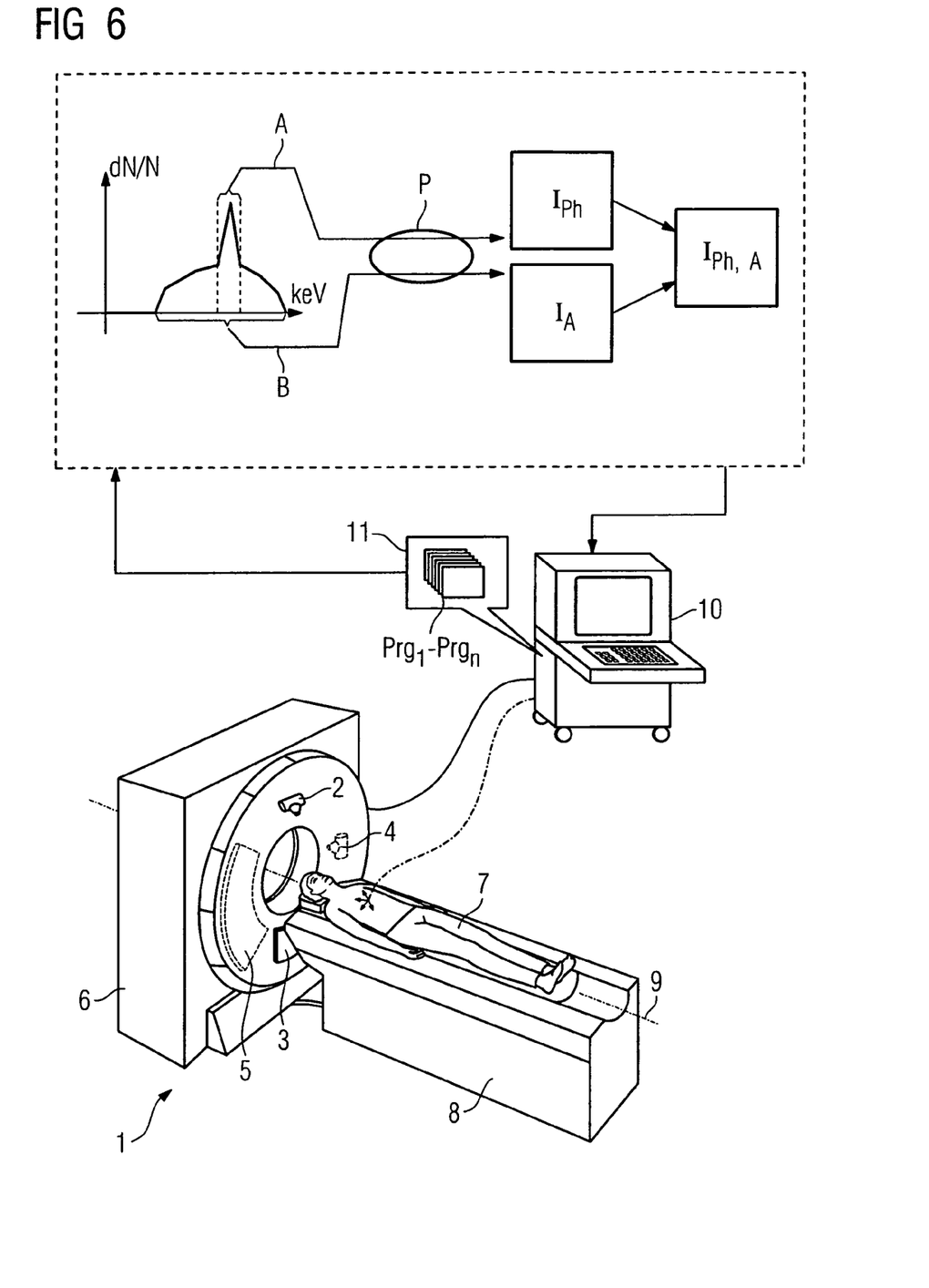
FIG. 6 shows a 3D illustration of an embodiment of an inventive CT system.

An embodiment of the inventive CT system for carrying out an embodiment of the inventive method is illustrated in FIG. 6. This shows the CT system 1, which has a first focus detector system with an x-ray tube 2 and an opposing detector 3 that are arranged on a gantry (not illustrated in more detail) in a gantry housing 6. A grating system in accordance with FIGS. 1 to 3 is arranged in the beam path of the first focus detector system 2, 3 such that the patient 7, who is located on a patient couch 8 that can be displaced along the system axis 9 can be pushed into the beam path of the first focus detector system and scanned there. The control of the CT system is carried out by an arithmetic and control unit 10 in which there are stored in a memory 11 programs $Prg_1$ to $Prg_n$ that carry out an embodiment of the above-described inventive method and reconstruct corresponding tomographic images from the measured radiation-dependent phase shifts and absorptions.

The carrying out of a variant of an embodiment of the inventive method is indicated schematically in the box represented by dashes. According thereto, the CT 1 uses a focus detector system 2, 3, or two focus detector systems 2, 3 and 4, 5, arranged with an offset, to determine in accordance with path A the phase shift, and thus the spatial distribution of the refractive indices $I_{Ph}$ with reference to a characteristic line in the x-ray spectrum illustrated. At the same time, the absorption behavior of the patient P is determined via the path B, and the spatial distribution of the absorption coefficients $I_A$ is thereby reconstructed.

If the examination of the patient relates to the coronary vessels, the scanning of the patient preferably takes place by using movement signals of the heart. For example, as is shown by dots and dashes in FIG. 6, an ECG derivation can be carried out, or the heart movement can also be detected with the aid of a kymogram. In the case of this particular variant of the scan, it is then only the data that are recorded in a phase as free from movement as possible which are then scanned for the purpose of visualization, are used for the purpose of visualization.

It is now possible to use the two sets of image data $I_{Ph}$ and $I_A$ in the synopsis $I_{Ph,A}$ to prepare a strongly differentiated assessment of plaque in vessel structures of the patient.

For example, known methods can firstly be used to segment the region of plaque in the vessel structure, and then the differentiated assessment of the plaque can be performed with the aid of the phase contrast images.

Figure 7:
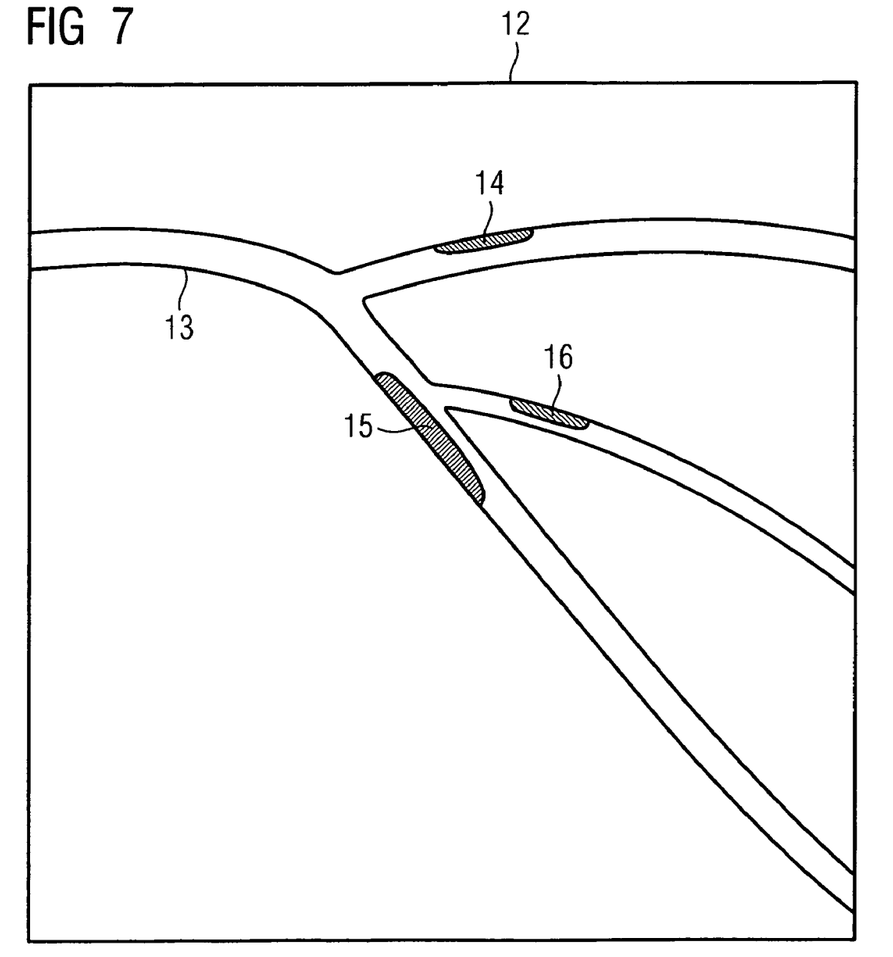
FIG. 7 shows an illustration of a coronary branching with different plaque forms.

The result of such a segmentation with subsequent assessment of the plaque is illustrated in FIG. 7. This shows an image detail 12 of a coronary region with the segmented coronary structure 13. Three edge regions, identified as plaque by absorption measurements, of the arteries 14, 15 and 16 are to be seen inside the coronary structure. On the basis of the strongly different refractive indices measured by tomographic phase contrast imaging, the regions 14 and 16 were identified as calcified, that is to say less pathogenic, plaque, while the region 15 was identified as soft plaque, which conceals a strong risk of infarction.

It goes without saying that the abovenamed features of the invention can be used not only in the combination respectively specified, but also in other combinations or on their own without departing from the scope of the invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for detecting and differentiating plaque in vessel structures of a patient, the method comprising:
reconstructing using a computed tomography system, including at least one focus detector system and, per focus detector system, at least one transradiated x-ray/optical grating, a spatial distribution of a refractive index in a region of vessel structures of the patient from detected projection data; and
highlighting at least one plaque form in a pictorial display on the basis of a previously known value range of the refractive index for the at least one plaque form.

2. The method as claimed in claim 1, further comprising:
associating the at least one plaque form with different value ranges of the refractive index; and
highlighting differently the at least one plaque form.

3. The method as claimed in claim 1, wherein the reconstructing of a spatial distribution is done using two focal detector systems arranged on a gantry in an angularly offset fashion.

4. The method as claimed in claim 1, wherein the reconstructing of a spatial distribution includes sweeping at two fan angles, one focus detector system including a fan angle relatively smaller than another focus detector system, and measuring the phase contrast with a relatively higher spatial resolution with the aid of a focus detector system with a at the relatively smaller fan angle.

5. The method as claimed in claim 1, further comprising:
generating quasi-coherent x-radiation for at least one of the focus detector systems.

6. The method as claimed in claim 1, wherein an analyzer detector system including an analyzer grating is used in at least one of the focus detector systems.

7. The method as claimed in claim 1, wherein use is made of at least one of the focus detector systems of an analyzer detector system that has a detector whose resolution is higher than the resolution of the measured pixels.

8. The method as claimed in claim 1, further comprising:
detecting the at least one of the plaque form and plaque formations is detected by comparing absorption data with refractive index data.

9. The method of claim 8, further comprising:
measuring exclusively the spatial distribution of refractive indices with a focus detector system; and
measuring exclusively the spatial distribution of the absorption coefficients with another focus detector system.

10. The method as claimed in claim 1, further comprising:
measuring the phase contrast for at least two different x-ray energies.

11. The method as claimed in claim 1, further comprising:
measuring absorption for at least two different x-ray energies.

12. The method as claimed in claim 10, wherein measuring of the phase contrast for at least two different x-ray energies is executed simultaneously with at least two focus detector systems.

13. The method as claimed in claim 1, further comprising:
measuring the phase contrast for at least two different x-ray energies to generate at least two measurements, wherein at least one of the measurements is carried out in a fashion triggered by the cardiac movement, use being made for visualization only of data in the rest phase of the heart.

14. The method as claimed in claim 4, further comprising:
generating quasi-coherent x-radiation at a larger fan angle by using at least one source grating between a focus and a patient.

15. A computed tomography (CT) system for detecting and differentiating plaque in vessel structures of a patient by phase contrast measurements, the system comprising:
at least one focus detector system, including at least one transradiated x-ray/optical grating to generate and detect x-radiation;
at least one analyzer detector system to measure a phase shift of impinging x-radiation;
an arithmetic and control system to control the CT system and reconstruct and evaluate measured results;
an output unit to output at least one of sectional and volume data;
a memory, including a look up table of refractive indices with stored value ranges and related plaque forms; and a marking apparatus to mark on an output sectional and volume data regions whose refractive indices lie in the value range for at least one plaque form.

16. The CT system as claimed in claim 15, wherein the memory of the computer system includes program code to cause the CT system to detect different plaque forms on the basis of different value ranges of the refractive index, and to display them in the differently highlighted fashion.

17. The CT system as claimed in claim 15, wherein the at least one focus detector system includes use is made two focus detector systems, arranged on a gantry in an angularly offset fashion.

18. The CT system as claimed in claim 17, wherein a first focus detector system includes a smaller fan angle than the second focus detector system and the first focus detector system includes a higher resolution analysis detector system, referred to the angular resolution, than the second focus detector system.

19. The CT system as claimed in claim 17, wherein a first focus detector system includes a smaller fan angle than the second focus detector system and only the first focus detector system includes an analysis detector system, whereas the second focus detector system is free from x-ray/optical gratings and serves only for measuring absorption data.

20. The CT system as claimed in claim 18, wherein the first focus detector system includes a substantially smaller focus than the second focus detector system.

21. The CT system as claimed in claim 15, wherein at least one focus detector system includes at least one source grating between focus and patient in order to generate quasi-coherent x-radiation.

22. The CT system as claimed in claim 15, wherein at least one focus detector system includes an analyzer detector system that has an analyzer grating.

23. The CT system as claimed in claim 15, wherein at least one focus detector system includes an analyzer detector system that including a detector whose angular resolution perpendicular to the grating lines of the phase grating at least three times as high as the resolution in the direction of the grating lines.

24. The CT system as claimed in claim 15, wherein at least one focus detector system includes an x-ray/optical grating whose grating lines are produced by standing ultra-sonic waves.

25. The CT system as claimed in claim 15, wherein at least one focus detector system includes an x-ray/optical grating that comprises a number of similar gratings arranged directly in sequence.

26. The CT system as claimed in claim 16, wherein the at least one focus detector system comprises two focus detector systems arranged on a gantry in an angularly offset fashion.

27. The CT system as claimed in claim 19, wherein the first focus detector system includes a substantially smaller focus than the second focus detector system.

* * * * *